United States Patent [19]

Roeschert et al.

[11] Patent Number: 5,247,096
[45] Date of Patent: Sep. 21, 1993

[54] PROCESS FOR PREPARING N-TERT-BUTOXYCARBONYLMALEIMIDE

[75] Inventors: Horst Roeschert, Ober-Hilbersheim, Fed. Rep. of Germany; Ralph Dammel, Coventry, R.I.; Georg Pawlowski, Wiesbaden; Klaus-Juergen Przybilla, Frankfurt am Main, both of Fed. Rep. of Germany

[73] Assignee: Hoechst Aktiengesellschaft, Frankfurt am Main, Fed. Rep. of Germany

[21] Appl. No.: 914,453

[22] Filed: Jul. 17, 1992

[30] Foreign Application Priority Data

Jul. 19, 1991 [DE] Fed. Rep. of Germany ....... 4124028

[51] Int. Cl.$^5$ ............................................ C07D 207/24
[52] U.S. Cl. .................................................... 548/531
[58] Field of Search .......................................... 548/531

[56] References Cited

U.S. PATENT DOCUMENTS

| 4,775,609 | 10/1988 | McFarland | 430/325 |
| 4,876,343 | 10/1989 | Hodges et al. | 548/531 X |
| 4,900,834 | 2/1990 | Kruger et al. | 548/531 X |

FOREIGN PATENT DOCUMENTS

| 0102450 | 3/1984 | European Pat. Off. . |
| 0234327 | 9/1987 | European Pat. Off. . |
| 0249139 | 12/1987 | European Pat. Off. . |
| 0404206 | 12/1990 | European Pat. Off. . |
| 0410606 | 1/1991 | European Pat. Off. . |
| 3817010 | 11/1989 | Fed. Rep. of Germany . |
| 2031538 | 11/1970 | France . |

OTHER PUBLICATIONS

Fieser, et al., Reagents for Organic Synthesis, vol. 4, (1974), p. 128.
Fieser, et al., Reagents for Organic Synthesis, vol. 8, (1980), pp. 57–58.
Fieser, et al., Reagents for Organic Synthesis, vol. 7, (1979), p. 91.
"Abstract of Papers" of the Polymer Society of Korea Fall National Meeting, Oct. 13–14, 1989, pp. 56–57.
Greene, "Protective Groups in Organic Synthesis" p. 232, New York, 1981.

*Primary Examiner*—Joseph Paul Brust
*Attorney, Agent, or Firm*—Foley & Lardner

[57] ABSTRACT

A process is described for preparing N-tert-butoxycarbonylmaleimide from maleimide and di-tert-butyl dicarbonate which comprises reacting maleimide with di-tert-butyl dicarbonate in the presence of a basic compound of the general formula I

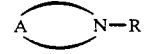
(I)

in which A represents the ring members required to complete a five- or six-membered saturated ring and R is $(C_1-C_4)$alkyl, in one stage to give the end product.

In a preferred embodiment, the compound of the general formula I is N-methylmorpholine.

The product is useful as a monomer for polymerization, with the styrene copolymers being particularly suitable for chemically reinforced radiation-sensitive mixtures.

13 Claims, No Drawings

PROCESS FOR PREPARING N-TERT-BUTOXYCARBONYLMALEIMIDE

BACKGROUND OF THE INVENTION

The present invention relates to a process for preparing N-tert-butoxycarbonylmaleimide from maleimide and di-tert-butyl dicarbonate.

N-tert-Butoxycarbonylmaleimide and copolymers thereof with styrene are reported in the "Abstract of Papers" of the Polymer Society of Korea Fall National Meeting, Oct. 13-14, 1989, pages 56-57. Homo- and copolymers with tert-butoxycarbonylmaleimide units are also disclosed in U.S. Pat. No. 4,775,609 and EP-A 0 234 327. They are prepared from the corresponding polymers without tert-butoxycarbonyl groups. Nothing is disclosed in these publications regarding processes for preparing monomeric tert-butoxycarbonylmaleimide.

tert-Butyl carbamates and their preparation from secondary amines and derivatives of carbonic acid are known. T. W. Greene, Protective Groups in Organic Synthesis, page 232, New York (1981) The introduction of the tert-butoxycarbonyl ("t-BOC") protective group into maleimide has to date involved considerable difficulties. When the reaction was attempted under basic conditions, for example, using an alkali, e.g., potassium carbonate; trialkylamines, e.g., triethylamine or pyridine; metal hydrides, e.g., NaH; alcoholates, e.g., potassium tert-butanolate, or organolithium compounds, e.g., tert-butyllithium, polymerization of the maleimide generally occurred.

The polymerization generally observed in basic media can be prevented by means of a multi-stage procedure. For this purpose, the C-C double bond of the maleimide is first "protected", for example, by a Diels-Alder reaction with cyclopentadienes. The reaction with di-tert-butyl dicarbonate in a basic medium can then take place in a subsequent stage. It is then necessary to introduce the double bond again, for example, by a retro-Diels-Alder reaction. However, such an expensive, multi-stage process is not very useful under practical conditions.

Acidic conditions also proved unsuitable since the t-BOC group is eliminated by acid. In an acidic medium, therefore, in the most favorable case, a dynamic equilibrium is established between the free and the t-BOC-protected amine groups.

SUMMARY OF THE INVENTION

It is therefore an object of the present invention to provide a one-stage process for preparing t-BOC-maleimide.

Thus, a process is provided for preparing N-tert-butoxycarbonylmaleimide from maleimide and di-tert-butyl dicarbonate which comprises reacting maleimide with di-tert-butyl dicarbonate in the presence of a basic compound of the general formula I:

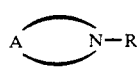
(I)

in which A represents the ring members required to complete a five- or six-membered saturated ring and R is $(C_1-C_4)$alkyl, in one stage to give the end product. In a preferred embodiment the compound of formula I is N-methylmorpholine.

Further provided is a process for polymerizing the t-BOC-maleimide to form mono- or copolymers which are useful in chemically reinforced radiation-sensitive mixtures.

These and other objects and features of the present invention will become apparent from the detailed description which follows.

DETAILED DESCRIPTION OF PREFERRED EMBODIMENTS

The invention thus relates to a process for preparing N-tert-butoxycarbonylmaleimide from maleimide and di-tert-butyl dicarbonate which comprises reacting maleimide with di-tert-butyl dicarbonate in the presence of a basic compound of the general formula I:

(I)

in which A represents the ring members required to complete a five- or six-membered saturated ring and R is $(C_1-C_4)$alkyl, in one stage to give the end product.

A is preferably a chain of 4 or 5 methylene groups. Particularly preferred chains are those in which at least one of the methylene groups is replaced by a nitrogen, oxygen or sulfur bridge atom. Suitable compounds of formula I are N-alkyl-pyrrolidine, N-alkyl- and N,N'-dialkyl-pyrazolidine, N-alkyl- and N,N'-dialkyl-imidazolidine, N-alkyl-isoxazolidine, N-alkyl-oxazolidine, N-alkyl-thiazolidine, N-alkyl- and N,N'-dialkyl-tetrahydro-[1,3,4]-oxadiazole, N-alkyl-piperidine, N-alkyl-2,2,6,6-tetramethyl-piperidine, N-alkyl- and N,N'-dialkyl-piperazine, N-alkyl-morpholine, N-alkyl-thiomorpholine, N-alkyl-tetrahydro-[1,2]oxazine. A most particularly preferred compound of the general formula I is N-methylmorpholine.

Partially unsaturated or benzo-fused basic compounds are also suitable, although they are not preferred: Examples of such compounds are: N-alkyl-2,5-and 2,3-dihydro-pyrrole, N-alkyl-2,3-dihydro-1H-indole, N-alkyl- and N,N'-dialkyl-2,3-dihydro-1H-indazole, N-alkyl- and N,N'-dialkyl-2,3-dihydro-1H-benzimidazole, N-alkyl-carbazole, N-alkyl-phenoxazine, N-alkyl-phenothiazine and 7- or 9-alkyl- or 7,9-dialkyl-8,9-dihydro-7H-purine. Alkyl in the above-specified compounds stands for $(C_1-C_4)$ alkyl.

The three components involved in the reaction are advantageously used in about equimolar amounts. The reaction is advantageously carried out in a solvent, such as ethyl acetate, acetonitrile, methylene chloride or tetrahydrofuran which does not react in an undesirable manner with the other components of the reaction mixture. The reaction temperature is held in a range of from 0°-50° C. It takes a relatively long time for the reaction to be completed. The reaction time is in general 20 to 120 hours, more particularly 50 to 100 hours. Optimum reaction temperature and reaction time depend on the solvent/base combination employed.

A large number of basic reaction conditions have been investigated and the desired result has not been obtained in any of those cases. Thus, it was surprising to one skilled in the art that a one-stage reaction, according to the present invention, in the presence of compounds of the general formula I, in particular N-methylmorpholine, takes place so smoothly and makes the desired product available in good yield.

The t-BOC-maleimide prepared according to the invention is suitable in particular as a monomer for polymerization. The polymers, mainly the copolymers, e.g., with styrene, are particularly suitable for so-called "chemically reinforced" radiation-sensitive mixtures (Osuch et al., SPIE, Adv. Res. Techn. and Proc., III 631 [1986] p. 68). The mixtures generally contain, in addition to a polymer which is soluble in aqueous alkaline solution after acid-catalyzed elimination of protective groups, at least one compound which forms an acid under the action of actinic radiation.

The use of polymeric compounds carrying t-BOC groups in light-sensitive coatings is described in, e.g., EP-A 102,450, EP-A 404,206, EP-A 249,139 and DE-A 3,817,010, the disclosures of which are hereby incorporated by reference. In principle, the maleimide can be provided with tert-butoxycarbonyl protective groups after polymerization. If such a procedure were carried out according to the present invention, i.e., by reacting a maleimide polymer and di-tert-butyldicarbonate in the presence of a compound of formula I, at most 70 to 90% of the maleimide units would be reacted. The results of this method are difficult to reproduce, and apparently identical conditions give derivatized polymers with different t-BOC contents.

Radiation-sensitive mixtures with polymers which contain derivatized as well as free maleimide units are not as desirable as those with only completely derivatized polymers. They have a shorter shelf life and the lithographic properties of recording materials produced therewith are poorer than those of recording materials which are produced using completely derivatized polymers. Therefore, it is desirable that derivatization according to the present invention is carried out prior to polymerization, thereby assuring that the polymer is completely derivatized.

The invention is further clarified by the following example, which is intended to be a purely illustrative use of the present invention.

EXAMPLE

A clear solution was prepared from
100 g of maleimide (1.03 mol),
225 g of di-tert-butyl dicarbonate (1.03 mol), and
2000 ml of ethyl acetate.

1.04 g (113 ml) of N-methylmorpholine (1.03 mol) were added dropwise to this solution over a period of 12 minutes. The temperature of the solution was kept at not more than 5° C. At this temperature, stirring was carried out for a further hour and the mixture was then allowed to warm up to room temperature and was allowed to stand for 80 hours at this temperature. After this time, the solution had a dark color.

For working up, the solution was poured into 1.5 l of ethyl acetate and the organic phase formed therefrom was washed four times with water and dried with sodium sulfate. The solvent was then stripped off and the remaining residue was dried. 179 g of a dark crystalline product (88% crude yield) were obtained in this manner.

The crude product was then dissolved at an elevated temperature in about 4.5 l of petroleum ether, and the hot solution was filtered three times over an active carbon/silica gel bed. The crystals which precipitated on cooling of the solution were then filtered off under suction, washed with petroleum ether and finally dried. 118 g of a product which was pure according to thin-layer chromatography and which had a melting point of 66° C. were obtained in this manner.

A further 15.3 g of pure product were obtained from the mother liquor by the following steps. The mother liquor was concentrated, the remaining residue was taken up in isopropyl ether and the resulting solution was filtered while hot over an active carbon/silica gel bed and was then cooled. The precipitated crystals were filtered off under suction, washed and dried.

The total amount of product was 133 g, corresponding to a yield of 65% of theory.

The product was characterized by $^1$H nuclear magnetic resonance spectroscopy ($^1$H-NMR), by thin-layer chromatography and by elemental analysis. The analytical results obtained were in agreement with those expected from the desired product, within the usual error limits.

$^1$H-NMR (CDCl$_3$), chemical shift in ppm on the $\delta$ scale: 6.7 [2 H] olefinic protons, 1.5 [9 H] protons of the tert-butyl group.

Elemental analysis: C$_9$H$_{11}$NO$_4$ (MW: 197.2).

|  | C | H | N |
|---|---|---|---|
| calculated: | 54.82% | 5.62% | 7.10% |
| found: | 55.0% | 5.8% | 6.9% |

Other embodiments of the invention will be apparent to those skilled in the art from a consideration of this specification or practice of the invention disclosed herein. It is intended that the specification and examples be considered exemplary only, with the true scope and spirit of the invention being indicated by the following claims.

What is claimed is:

1. A one-step process for preparing N-tert-butoxycarbonylmaleimide from maleimide and di-tert-butyl dicarbonate, comprising the step of reacting maleimide with about an equimolar amount of di-tert-butyl dicarbonate in the presence of an about equimolar amount of a basic compound, which is (a) a compound of the formula I

in which A represents the ring members selected from the group consisting of carbon, oxygen, nitrogen, and sulfur atoms required to complete a five- or six-membered saturated or partially unsaturated ring and R is (C$_1$-C$_4$)-alkyl, or (b) a compound selected from N-alkyl-2,3-dihydro-1H-indole, N-alkyl- and N,N'-dialkyl-2,3-dihydro-1H-indazole, N-alkyl- and N,N'-dialkyl-2,3-dihydro-1H-benzimidazole, N-alkyl-carbazole, N-alkyl-phenoxazine, N-alkyl-phenothiazine, and 7- or 9-alkyl- or 7,9-dialkyl-8,9-dihydro-7H-purine at a temperature in the range of from 0° to 50° C., for a reaction time suitable to give N-tert-butoxycarbonylmaleimide.

2. The process as claimed in claim 1, wherein A is a chain of 4 or 5 methylene groups.

3. The process as claimed in claim 1, wherein A is a chain of 4 or 5 methylene groups wherein at least one of the methylene groups is replaced by a nitrogen, oxygen or sulfur bridge atom.

4. The process as claimed in claim 3, wherein the compound of the formula I is N-methylmorpholine.

5. The process as claimed in claim 1, wherein the reaction is carried out in a solvent which does not react in an undesirable manner with the other components of the reaction mixture.

6. The process as claimed in claim 5, wherein the solvent used is ethyl acetate.

7. The process as claimed in claim 1, wherein the compound of formula I is selected from the group consisting of N-alkyl-2,5- and 2,3-dihydro-pyrrole, N-alkyl-pyrrolidine, N-alkyl- and N,N'-dialkyl-pyrazolidine, N-alkyl- and N,N'-dialkyl-imidazolidine, N-alkyl-isoxazolidine, N-alkyl-oxazolidine, N-alkyl-thiazolidine, N-alkyl- and N,N'-dialkyl-tetrahydro-[1,3,4]-oxadiazole, N-alkyl-piperidine, N-alkyl-2,2,6,6-tetramethyl-piperidine, N-alkyl- and N,N'-dialkyl-piperazine, N-alkyl-morpholine, N-alkyl-thiomorpholine, and N-alkyl-tetrahydro-[1,2]-oxazine.

8. The process as claimed in claim 1, wherein the compound of formula I is selected from the group consisting of N-alkyl-2,3-dihydro-1H-indole, N-alkyl- and N,N'-dialkyl-2,3-dihydro-1H-indazole, N-alkyl- and N,N'-dialkyl-2,3-dihydro-1H-benzimidazole, N-alkyl-carbazole, N-alkyl-phenoxazine, N-alkyl-phenothiazine, and 7- or 9-alkyl-or 7,9-dialkyl-8,9-dihydro-7H-purine.

9. The process as claimed in claim 5, wherein the solvent is selected from the group consisting of acetonitrile, methylene chloride, and tetrahydrofuran.

10. The process as claimed in claim 1, wherein the reaction time is from 20 to 120 hours.

11. The process as claimed in claim 1, wherein the reaction time is from 50 to 100 hours.

12. The process as claimed in claim 6, wherein the compound of formula I is N-methyl morpholine.

13. The process as claimed in claim 12, wherein the temperature is not more than 5° C.

* * * * *